United States Patent [19]
Dunn et al.

[11] Patent Number: 5,766,432
[45] Date of Patent: Jun. 16, 1998

[54] METHOD AND DEVICE FOR ELIMINATING ELECTRODE DRIFT

[75] Inventors: Raymond M. Dunn, Shrewsbury; Robert Harrington, Westboro; Robert Peura, Princeton; Stevan Kun, Worcester, all of Mass.

[73] Assignees: University of Massachusetts, Boston; Worcester Polytechnic Institute, Worcester, both of Mass.

[21] Appl. No.: 632,330

[22] Filed: Apr. 17, 1996

[51] Int. Cl.⁶ ............................................. G01N 27/26
[52] U.S. Cl. ................... 204/412; 128/637; 128/640; 204/406; 204/420; 204/433; 204/435
[58] Field of Search ........................ 204/412, 406, 204/420, 433; 205/787.5; 128/635, 637, 640

[56] References Cited

U.S. PATENT DOCUMENTS

| | | |
|---|---|---|
| 4,133,732 | 1/1979 | Boeke . |
| 4,155,814 | 5/1979 | Tejfalussy et al. . |
| 4,404,065 | 9/1983 | Matson . |
| 4,647,362 | 3/1987 | Watanabe . |
| 4,686,011 | 8/1987 | Jäckle . |
| 4,748,562 | 5/1988 | Miller et al. .................. 128/635 |
| 4,780,663 | 10/1988 | Mulder ........................ 73/304 R |
| 4,886,584 | 12/1989 | Cheng . |
| 4,912,417 | 3/1990 | Giggoney et al. . |

*Primary Examiner*—John P. Lacyk
*Assistant Examiner*—Rosiland Kearney
*Attorney, Agent, or Firm*—Fish & Richardson P.C.

[57] ABSTRACT

A pH-measuring method and device for monitoring and then correcting for electrode drift is provided. The device includes a pH-measuring electrode and more than one reference electrode. During operation, the pH-measuring device is place in contact with a sample. The pH value measured at each electrode pair is due to the electrical potential difference between the pH electrode and the reference electrode. The maximum and minimum pH values are determined, and then the remaining pH values are averaged together to generate an overall average pH. The maximum and minimum pH values are subtracted from the average pH to generate a difference which is then compared to a user-defined drift level to determine if a particular electrode is deficient. The pH values from deficient electrodes are not considered when the overall pH of the sample is determined.

9 Claims, 3 Drawing Sheets

METHOD AND DEVICE FOR ELIMINATING ELECTRODE DRIFT

BACKGROUND OF THE INVENTION

This invention relates to systems for measuring ph, particularly pH of tissue samples.

A tissue's viability is indicated by its pH. This is because tissue viability depends on the amount of blood flowing within the tissue. Obstruction of blood flow induces ischemia, a condition that leads to hydrogen ion accumulation and corresponding acidosis within the tissue These processes reduce the tissue's pH. Measurement of pH can therefore be used to diagnose both the degree of ischemia and viability of the tissue.

Tissue pH is typically measured during surgical procedures where the tissue is removed from one part of the body and transplanted to another. Incoming blood flow to the tissue is severed and then restored during this procedure, making the tissue particularly susceptible to ischemia. As an example, in microvascular reconstructive surgery, a surgeon first selects a site of tissue (i.e., a donor site) which is anatomically similar to the tissue requiring reconstruction. The surgeon then separates the donor site tissue from the adjoining tissue by severing the underlying blood vessels. This segment of tissue is called a "flap". Using microsurgery, the flap is attached to a new site by repairing the severed blood vessels. This process restores circulation to the flap and completes the procedure. Flaps can be composed of, e.g., skin, muscle, bone, and nerve tissues.

Once reattached, the flap either remains viable or become ischemic. Initially, the flap can be slightly acidotic because its circulation is not completely restored; the flap then returns to a normal state upon return of blood flow. In the event that blood flow is not adequately restored, the tissue flap becomes fully acidotic and eventually dies.

The flap's pH is typically measured by determining the electrical potential between a hydrogen ion activity-measuring electrode in contact with the flap and a reference electrode in electrical contact with a portion of the patient's body. The electrical potential is then correlated to the tissue's pH using the well-known Nernst equation.

While effective in measuring pH over short time periods, conventional pH-measuring devices are impaired by time-dependent drifts in the electrical potential measured at either electrode. These drifts, in turn, decrease the accuracy of the device's long-term pH measurement. Reference electrodes are especially prone to drift when used for time periods greater than 24 hours.

SUMMARY OF THE INVENTION

The invention provides a method and device for measuring pH and correcting for electrode drift over long-term and short-term time periods. In one aspect, the method includes the step of first contacting a sample (e.g., a tissue) with a pH-measuring device containing a pH-measuring electrode and a plurality of reference electrodes. Preferably, the pH-measuring electrode is inserted in the tissue, and the references electrodes are in electrical contact with the patient's body. Together, each reference electrode and the pH-measuring electrode form a separate "electrode pair" which measures a pH value. During operation, the method averages at least two of the pH values together to determine an average pH, and calculates the difference between certain pH values and the average pH. The method then compares these differences to a user-defined drift level (i.e., an "acceptable" level of pH drift, defined below) for a predetermined drift time period (also defined below). A difference in pH greater than the predetermined drift level measured for a time period greater than the drift time period indicates a deficient electrode. The pH of the sample is determined by analyzing (e.g., by averaging) the pH values from all the electrode pairs including non-deficient reference electrodes.

In preferred embodiments, the method determines maximum and minimum pH values between the measuring and averaging steps. In this case, all the pH values except the maximum and minimum pH values are averaged together to determine the average pH. The method then calculates differences between the average pH and the maximum and minimum pH values. Based on these differences, the method determines if any of the reference electrodes are deficient, and then analyzes the pH values from the non-deficient electrodes to determine the pH.

In another aspect, the invention provides a method for monitoring drift of an electrode in an electrode-containing device using the steps described above. In this method, electrical signals, rather than pH values, are processed to determine if a reference electrode is deficient.

The drift time period and drift level are preferably determined and supplied by the user prior to the contacting step. The drift level and drift time are preferably numbers stored in the memory of a computer or microprocessor interfaced with the pH-measuring device. The drift level is typically between 0.01 and 0.5 pH units, and the drift time is typically between 10 seconds and 1 hour. In preferred embodiments, the drift level and drift time are, respectively, about 0.25 pH units and about 30 minutes. Both the drift level and drift time can be adjusted for different procedures.

In preferred embodiments, the deficient electrode is manually removed from the sample during the excluding step, and then replaced with a new electrode. The deficient electrode can also be electronically removed from the sample during the excluding step. In this case, "electronically removed" means that electronic means are used to prevent the deficient electrode from supplying a signal for the subsequent calculations. For example, the electrode's signal may be disregarded by the computer or microprocessor using a computer program. The signal is disregarded during the time period that the electrode is considered to be deficient. The electrically removed deficient electrode can then be electronically replaced with a new electrode following the excluding step. Here, "electronically replaced" means the opposite of "electronically removed" i.e., a new signal from a new electrode is received and processed by the computer or microprocessor using a computer program.

The pH-measuring method is carried out with an electrode-containing device. The device preferably features multiple electrode pairs, each containing the pH-measuring electrode in electrical contact with a separate reference electrode. A microprocessor is in electrical contact with each electrode pair. The microprocessor is programmed to perform the averaging, calculating, comparing, determining, and, optionally, excluding steps described above. The microprocessor can contain the drift time period and drift level in its memory.

Each of the reference electrodes is preferably a non-invasive electrode or an electrical contact, such as a cutaneous (e.g., skin-surface) electrode. The pH-measuring electrode is preferably a glass electrode.

The invention has a number of advantages. In particular, the pH-measuring device minimizes the effects of reference electrode drift. This increases the accuracy of both the pH measurement and the assessment of a tissue's viability. This is particularly desirable in situations where it is necessary to measure pH for long periods of time. For example, in microvascular reconstructive surgery, a tissue's pH is monitored for time periods greater than 24 hours; an accurate assessment of pH is needed to monitor the onset of ischemia. The pH-measuring device of the invention can be used during surgery to ensure that the underlying vessels are properly attached, and after surgery to monitor restoration of the tissue's viability.

The device can also be used in a wide range of other applications. For example, the device can help diagnose pH-dependent maladies, such as Compartment Syndrome. This condition is characterized by an increased pressure within a limited space of tissue. The pressure increase compromises the circulation and function of the tissue, resulting in an increased pH. The device can also be used during fetal monitoring, myocardial pH monitoring, pH monitoring of gut mucosa, monitoring of compromised tissue, measurement of the lateral aspect of tissues (e.g., the thigh), monitoring of shock and hypoxia, assessment of the pH of open wounds, and assessment of the extent of muscle damage after a severe burn injury. The device can also be used in other applications, such as for measuring the pH in food and in chemical, biological, and pharmaceutical systems.

In general, the device is minimally invasive, easy to use, and can be readily assembled from commercially available, off-the-shelf components.

Unless otherwise defined, all technical and scientific terms used herein have the same meaning as those commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated herein by reference in their entirety. In case of conflict, the present application, including definitions, will control. In addition, the materials, methods, and examples are illustrative only and not intended to be limiting.

Still other advantages of the invention will be apparent from the following detailed description, and from the claims.

DETAILED DESCRIPTION pH-Measuring Method

Figure 1:
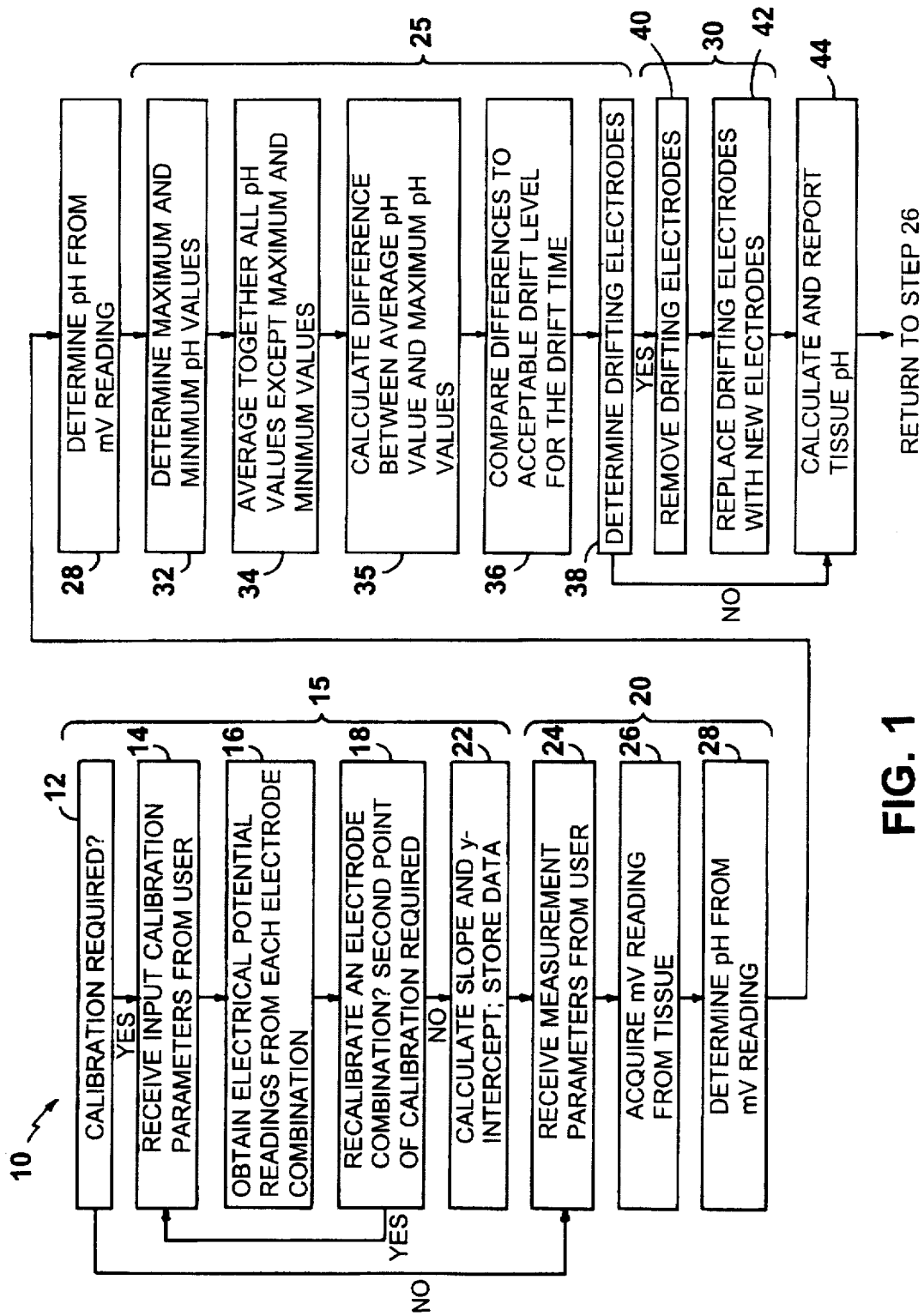
FIG. 1 is a flow chart showing a series of steps for measuring pH according to the pH-measuring method of the invention.
Figure 3:
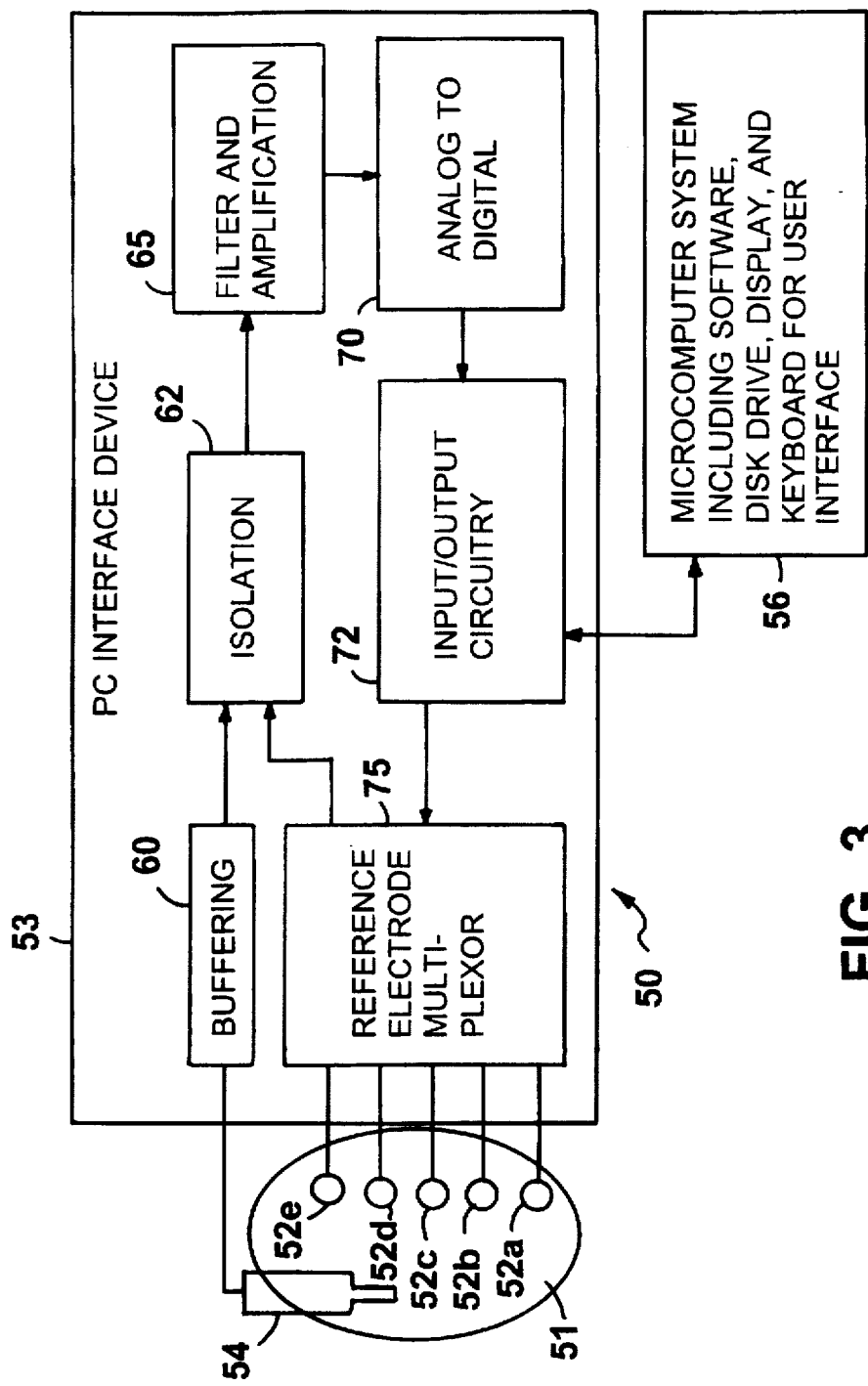

FIG. 1 shows a flow chart illustrating a pH-measuring method for determining the pH of a tissue. The method includes: i) a series of calibration steps 15 for calibrating a pH-measuring device (containing a single pH-measuring electrode and multiple reference electrodes, as shown in FIG. 3); ii) a series of measurement steps 20 for measuring the pH of the tissue; iii) a series of analysis steps 25 for determining any drift in the reference electrodes of the pH measuring device; and, iv) a series of correction steps 30 for removing the drifting electrodes from the pH-measuring device.

By determining and compensating for any drifting reference electrodes in the pH-measuring device, the method provides accurate pH measurements over both long and short time periods.

The pH-measuring method employs a computer or microprocessor connected directly to the pH-measuring device. Each step in the method can be implemented in either hardware, software, or a combination of the two.

The calibration steps 15 are used to calibrate each reference/pH-measuring electrode pair in the pH-measuring device. Whether or not calibration is necessary is determined (step 12) during the calibration steps 15. If calibration is necessary, a series of input calibration parameters (step 14) are received from a user and used to calibrate each electrode pair. Calibration parameters are data indicating the actual pH of a reference sample. Electrical potential readings for each electrode pair are then obtained from the reference sample (step 16), and then compared to the calibration parameters. During step 18, electrode pairs can be recalibrated if erroneous readings occur; additional calibration points can also be determined by adjusting the pH of the reference sample, and then remeasuring the electrical potential.

Calibration is usually necessary if the pH-measuring device is being used to measure a new sample, or if the device is being used for the first time. Previously determined calibration values for each electrode pair can be stored in memory in the computer or microprocessor, making it unnecessary to perform new calibration steps.

Electrical potential and pH data obtained during steps 14, 16, and 18 are linearly related according to the Nernst equation. These data are analyzed (step 22) to determine a series of calibration factors (i.e., the slope and y-intercept) relating the electrical potential measured at each electrode pair to the reference sample pH. Once determined, the calibration factors are stored in memory and used during the measurement steps 20 and analysis steps 25 to determine the tissue's pH. The device can be recalibrated if either the slope or y-intercept appear to be unstable or invalid.

Measurement parameters such as the measurement time, time intervals for individual pH measurements, the number of electrodes, the drift time, the drift range, and the name of a data file used to store the measured pH values are received (step 24) during the measurement steps 20. Electrical potential readings are then obtained (step 26) by inserting the pH-measuring electrode in a tissue sample and attaching the reference electrodes to different (but preferably closely spaced) locations on the patient's body. All the reference electrodes are preferably cutaneous electrodes (described in detail below) or other non-invasive electrodes or electrical contacts attached to the surface of the skin.

The electrical potential is determined by first measuring a voltage at the pH-measuring electrode and each reference electrode. These voltages are processed (e.g., buffered, isolated, filtered, and amplified) prior to calculating the voltage difference between the pH-measuring electrode and each reference electrode. The pH for each electrode combination is determined (step 28) by relating the electrical potential measured with each electrode pair to the calibration factors determined during step 22.

The amount of drift in each reference electrode is determined during the analysis steps 25. This is preferably done by first determining the maximum and minimum pH values measured by the electrode pairs (step 32). An average pH is then calculated by averaging together all the pH values except the maximum and minimum values (step 34). The difference between the maximum and minimum pH values and this average is then calculated (step 35) and compared to a predetermined, user-defined drift level (step 36). The drift level is an amount of drift, given in pH units, which is acceptable for an electrode.

A reference electrode "drifts" (and is thus considered to be deficient) if the difference between the pH value it measures and the average pH, measured during step 34, falls outside the user-defined drift level for a select "drift time" (step 38). Conversely, a reference electrode is "acceptable" if the difference between the pH reading from its electrode pair and the average pH value does not fall outside the drift level for a time exceeding the drift time. The values of the drift level and the drift time are predetermined by the user, and depend on the tissue type, the condition of the tissue, and the nature of the procedure being performed. In general, the drift level is typically set between about 0.01 and 0.5 pH units; most preferably, the drift level is about 0.25 pH units. The drift time is typically between 10 seconds and one hour, and is most preferably about 30 minutes. The time period and drift level can be set at longer or shorter times, or high and lower values, deemed acceptable by the user.

Deficient reference electrodes are removed from the pH-measuring device (step 40) during the correction steps 30. The deficient electrode is then replaced with a new electrode (step 42) by the user. Acceptable reference electrodes are kept in the pH-measuring device, and the pH value measured by their electrode pairs are used to calculate and report a final, overall average pH (step 44) of the sample. The method can then be repeated and used to acquire new potential readings from the electrodes (step 26).

Figure 2:
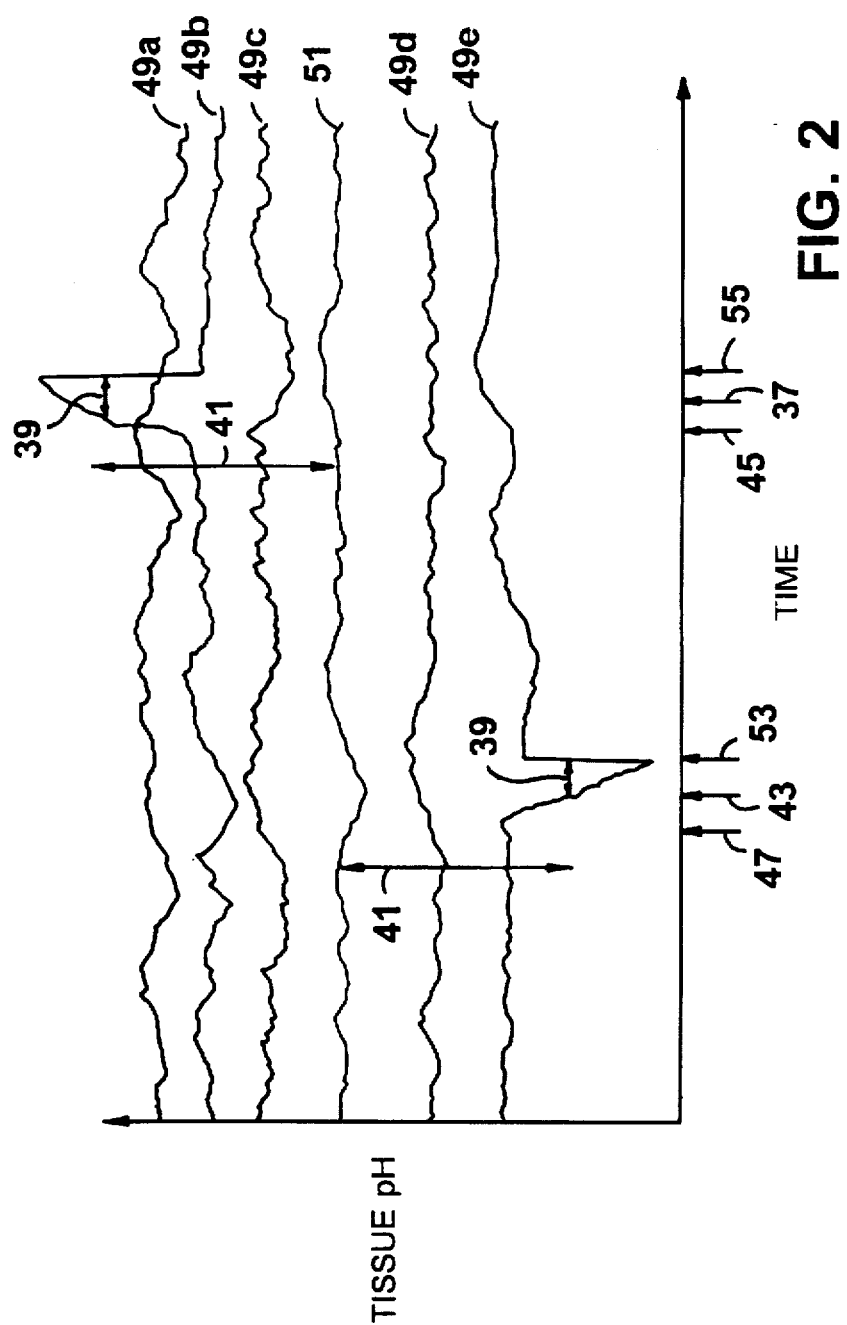
FIG. 2 is a schematic graph plotting a set of time-dependent electrical signals measured using the pH-measuring device of the invention; and, FIG. 3 is a schematic drawing showing the electrical components the pH-measuring device of the invention.

The benefit of the method described above is indicated by FIG. 2, which shows a schematic graph plotting time-dependent tissue pH measured with the pH-measuring device. The pH-measuring device features five reference electrodes, each of which generates a separate, time-dependent pH measurement. Each measurement is plotted as a separate curve 49a–e in the graph. The maximum and minimum pH values are represented, respectively, by curves 49a and 49e. A curve 51 showing the average of the three curves 49b–d representing pH values other than the maximum and minimum values is also plotted in the figure.

Time points where certain reference electrodes begin to drift are indicated in the graph by arrows 47 and 45. Acceptable drift levels and drift times (described above) are indicated by the arrows 41 and 39, respectively. Curves 49a, 49c, and 49d exhibit only minor time-dependent pH fluctuations, never falling outside the acceptable drift levels for time periods exceeding the drift time. The reference electrodes from the electrode pairs used to make these measurements are therefore acceptable, and are not replaced during the pH-measuring method.

In contrast, curves 49b and 49e show more severe pH fluctuations due to reference electrode drift. The pH indicated by curve 49e begins to decrease sharply at the time indicated by arrow 47. This decrease is due to reference electrode drift. The pH value falls outside the acceptable drift level at a time indicated by the arrow 43, and does not return to a value within the acceptable drift level (indicated by the arrow 41) before the drift time (indicated by the arrow 39). According to the method described above, the reference electrode used to measure curve 49e is unacceptable, and is replaced at a time indicated by the arrow 53. Replacing the deficient electrode returns the curve to its original, pre-drift level.

A similar situation occurs with curve 49b. In this case, the reference electrode begins to drift at a time indicated by the arrow 45, causing the measured pH to increase. The pH value falls outside the acceptable drift level at a time indicated by the arrow 37. The reference electrode used to make the pH measurement is unacceptable, and is replaced when the curve fails to return to an acceptable pH value during the drift time (indicated by the arrow 39). This causes a sudden decrease in the measured pH and returns the curve to its pre-drift level.

pH-Measuring Device

FIG. 3 is a schematic drawing showing a pH-measuring device 50 for measuring the pH of a tissue 51 using the method described above. The device 50 includes five separate reference electrodes 52a–e and a pH-measuring electrode 54. The reference electrodes 52a–e are attached to different locations on the surface of the tissue 51; the pH-measuring electrode 54 is inserted directly into the newly transplanted tissue 51. Each reference electrode and the pH-measuring electrode are in electrical contact with a separate channel located on a computer 56, e.g., a personal computer or a microprocessor.

The pH-measuring electrode 54 is preferably an ion-selective electrode, such as a glass microelectrode. These types of electrodes do not consume nor contaminate the underlying tissue, and require little tissue preparation. A typical glass microelectrode consists of a glass bulb (having a thickness of about 50–200 microns) filled with an electrolyte solution. Included in the electrolyte solution is a metal electrode (frequently Ag-AgCl). Glass electrodes are manufactured by, for example, Microelectrodes, Inc. of Londonderry, N.H.

Reference electrodes are preferably cutaneous, skin-surface electrodes. These electrodes are preferred because they exhibit low impedance, a large contact area, small amounts of electrical noise due to tissue motion, and can be easily adhered to the patient without requiring significant tissue preparation or penetration. Such electrodes are available from, for example, Applied Biosensors, Inc. of Flanders, N.J.

A computer interface device 53 processes electrical signals from the reference 52a–e and pH-measuring 54 electrodes and sends these signals to the personal computer 56 for analysis. The interface device 53 includes buffering 60, isolation 62, and filtering and amplification 65 stages, an analog-to-digital (AD) converter 70, input/output control circuitry 72, and a reference electrode multiplexor 75. During operation, analog signals from each reference electrode are sent via the reference electrode multiplexor 75 to the isolation stage 62. Software in the personal computer 56 and the input/output control circuitry 72 control the timing of the multiplexor 75. The analog signal from the pH-measuring electrode is sent to the high-impedance input buffer 60 prior to being sent to the isolation stage 62. The buffer 60 typically operates in a common mode of $10^{15}$ $\Omega$ which is necessary because of the high source impedance of the pH-measuring electrode. The output from the isolation stage 62 is then sent to the filtering and amplification stage 65. This stage functions as a low-pass filter (having an adjustable cut-off frequency typically near 0.5 Hz) to filter out 60-Hz noise from fluorescent lights and ac power lines, high electromagnetic frequencies, and low frequencies caused by electrode movement on the tissue. The stage also differentially amplifies (with a gain of about 20) the electrical potential difference (in mV) between the reference electrodes 52a–e and the pH-measuring electrode 54.

The output from the filtering and amplification stage 65 is sent to the analog-to-digital (AD) converter 70. There, the mV analog signal is digitized and sent via the control circuitry 72 to the personal computer 56. The digitized signal is processed with the computer 56 as described above to determine the pH measured by each of the five electrode pairs. The computer then determines which reference electrode is drifting and then eliminates the resulting pH value from the overall average. A new electrode can then replace the deficient electrode and supply a new pH value to the overall average.

Other Embodiments

Other embodiments are within the scope of the invention. In particular, steps in the pH-measuring method which are normally performed manually can be automated and performed by a computer. For example, deficient, drifting electrodes can be "removed" by a computer by shutting off the channels which receive and process the drifting electrical signals. The deficient electrode is not included in the calculation for determining the pH, and the measurement is completed without having to alert an operator. Any other embodiment wherein a drifting electrode is identified and replaced with a properly functioning electrode to calculate the average pH is within the scope of the invention.

The pH-measuring device can take any form. For example, the device can be integrated in a single hand-held or body-worn unit. This unit, in turn, can be used for short and long-term pH measurements, and be used by the patient outside of the hospital. The pH-measuring device can also include a user interface which alerts the user to the presence of a drifting electrode. Such an interface, for example, would be valuable for alerting hospital personnel to the presence of a drifting electrode used to measure a tissue. The pH-measuring device can also be accessed using a modem so that measurements can be analyzed off-site.

A pH-measuring system can include a single set of electrode pairs for measuring the pH of a single sample or patient, or multiple sets of electrode pairs for measuring multiple samples or patients. The system can also include multiple pH-measuring electrodes and reference electrodes for measuring the pH of a single sample. When the number of reference and pH-measuring electrodes are equal, each pH-measuring electrode can be combined with a separate reference electrode to form an electrode pair. When there are more reference electrodes than pH-measuring electrodes, electrode pairs can be formed by combining any one of the pH-measuring electrodes with one or more of the reference electrodes.

In still other embodiments, the pH-measuring method and device can be used to correct for drift in the pH-measuring electrode (rather than only the reference electrode). Drift in the pH-measuring electrode is typically indicated when all the electrode pairs begin to drift at a particular time.

Each electrical component of the pH-measuring device can be replaced with a alternate component performing the same or a similar electrical function. For example, the pH-measuring and reference electrodes can take any form. Any electrode which measures pH can be used. Other electrodes which can be used include metal electrodes, suction electrodes, floating electrodes, flexible electrodes, and dry electrodes.

Likewise, any method step can be replaced with one or more steps, or removed from the method, to correct for the drift in either the reference pH-measuring electrodes. For example, statistical methods other than calculating the average and standard deviation of each electrode measurement can be used. Differences can also be calculated between the average pH and each of the pH values, rather than just between the average pH and the maximum and minimum values.

During operation, the reference electrodes can be attached at any location on the patient's body, while the pH-measuring electrode is inserted in the tissue to be measured. When used to measure the pH of a tissue, these locations are preferably within the same general area (e.g., separated by a few centimeters). The pH-measuring method and device can also be used to measure the pH of samples other than tissue. Such samples include non-biological samples which are either liquids or solids.

Similarly, the method and device can be used to account for electrode drift in applications other than those used to measure pH. The method, for example, can be used to monitor and correct the voltage or electrical potential of an electrode or an electrode pair. In this case, the device is not calibrated (and the method does not include a step) to calculate pH, and drift in the electrical potential of the electrode pair is monitored as described above.

Still other embodiments are within the scope of the following claims.

What is claimed is:

1. An electrode-containing device comprising:

a measuring electrode;

a plurality of reference electrodes in electrical contact with said measuring electrode, wherein each of the reference electrodes forms an electrode pair when electrically contacted with the measuring electrode; and, a microprocessor in electrical contact with each electrode pair, said microprocessor being programmed to:
   receive an electrical signal from each electrode pair;
   average together at least two of the electrical signals to determine an average electrical signal;
   calculate an electrical signal difference between at least one electrical signal and the average electrical signal; and
   compare each electrical signal difference to a predetermined drift level, wherein an electrical signal difference greater than the drift level existing for a time period greater than a predetermined drift time indicates a deficient reference electrode.

2. The device of claim 1, wherein said measuring electrode is a glass electrode.

3. The device of claim 1, further comprising a plurality of measuring electrodes each being in electrical contact with at least one of said plurality of reference electrodes.

4. The device of claim 1, wherein the measuring electrode is a pH-measuring electrode.

5. The device of claim 4, wherein the electrical signal received by the microprocessor indicates a pH value.

6. The device of claim 5, wherein the microprocessor is programmed to:

average together at least two of the electrical signals to determine an average pH;

calculate a difference between at least one pH value and the average pH; and determine the pH of the sample by analyzing the pH values from the non-deficient reference electrodes.

7. The device of claim 1, wherein each of said reference electrodes is a non-invasive electrode or an electrical contact.

8. The device of claim 7, wherein each of said reference electrodes is a cutaneous or sub-cutaneous electrode.

9. The device of claim 8, wherein said cutaneous electrode is a skin-surface electrode.

* * * * *